United States Patent [19]

Fujikawa et al.

[11] Patent Number: 4,965,380
[45] Date of Patent: Oct. 23, 1990

[54] PROCESS FOR PREPARATION OF ASYMMETRIC TRIORGANOTIN HALIDE

[75] Inventors: Masazumi Fujikawa, Ibaraki; Hideo Haneda, Kobe, both of Japan

[73] Assignee: Nitto Kasei Co., Ltd., Osaka, Japan

[21] Appl. No.: 412,322

[22] Filed: Sep. 25, 1989

[30] Foreign Application Priority Data

Sep. 28, 1988 [JP] Japan .................................. 63-245269

[51] Int. Cl.$^5$ .............................. C07F 7/08; C07F 7/22
[52] U.S. Cl. ....................................................... 556/12
[58] Field of Search ........................................... 556/12

[56] References Cited

U.S. PATENT DOCUMENTS

| | | | |
|---|---|---|---|
| 2,920,060 | 1/1960 | Merker | 556/12 X |
| 3,043,858 | 7/1962 | Merker | 556/12 |
| 4,774,235 | 9/1988 | Omazaki et al. | 556/12 X |

Primary Examiner—Paul F. Shaver
Attorney, Agent, or Firm—Wenderoth, Lind & Ponack

[57] ABSTRACT

A process for the preparation of an asymmetric triorganotin halide which is represented by the general formula [III]

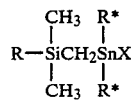

[III]

wherein R represents alkyl or phenyl, R* represents cyclohexyl or neophyl, and X represents a chlorine or bromine atom, which comprises reacting in the presence or absence of an inert organic solvent an asymmetric tetraorganotin compound of the general formula [I]

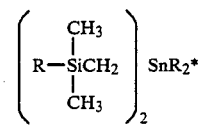

[I]

with a tin (IV) halide of the general formula [II]

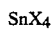

[II]

in approximately equimolar amounts to yield a reaction mixture including compounds of the general formula of [III] and [IV]

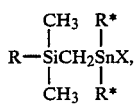

[III]

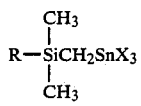

[IV]

and subsequently, without the isolation of the asymmetric triorganotin halide [III], reacting the reaction mixture with substantially twice the molar amount, based on monoorganotin trihalide [IV], of an ether solution of organomagnesium halide of the general formula of [V]

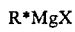

[V]

5 Claims, No Drawings

PROCESS FOR PREPARATION OF ASYMMETRIC TRIORGANOTIN HALIDE

This invention relates to a process for the preparation of an asymmetric triorganotin halide.

An asymmetric triorganotin halide has biological activity per se and can effectively protect plants from damage from mites.

As a process for the preparation of an asymmetric triorganotin halide, a process is known in which the phenyl radical is severed by reacting an equimolar amount of halogen with an asymmetric tetraorganotin including a phenyl radical (Japanese Patent Laid-Open Application No. 149689/1987).

Also, in general, the preparation of a symmetric or an asymmetric triorganotin halide has been tried by reacting two moles of the same or different kinds of organomagnesium halide with one mole of monoorganotin trihalide.

However, the process described in Japanese Patent Laid-Open Application No. 149689/1987 requires five reaction steps starting from a diorganotin dihalide as a raw material and therefore has a disadvantage in the length of the process and in a lowered yield.

Also, in any conventional process of reacting two moles of the same or different kind of organomagnesium halide with one mole of monoorganotin trihalide, tetraorganotin is mainly formed and the intended triorganotin halide is only obtained in a low yield.

According to the present invention, it has been discovered that asymmetric triorganotin halides can be obtained in high yields and high purities by reacting an asymmetric tetraorganotin compound with a tin (IV) halide to produce a mixture of asymmetric triorganotin halide and monoorganotin trihalide, and allowing the monoorganotin trihalide (without isolating the asymmetric triorganotin halide from the reaction mixture) to react with a particular organomagnesium halide.

Thus, the present invention provides a process for the preparation of an asymmetric triorganotin halide which is represented by the general formula [III]

$$\begin{array}{c} CH_3 \ \ R^* \\ | \ \ \ \ | \\ R-SiCH_2SnX \\ | \ \ \ \ | \\ CH_3 \ \ R^* \end{array} \qquad [III]$$

wherein R represents alkyl, preferably having 1 to 8 carbons, or phenyl, R* represents cyclohexyl or neophyl, and X represents a chlorine or bromine atom, which comprises reacting in the presence or absence of an inert organic solvent an asymmetric tetraorganotin compound of the general formula [II]

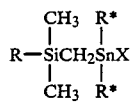

wherein R and R* are as defined above, with a tin (IV) halide of the general formula [II]

$$SnX_4 \qquad [II]$$

wherein X is as defined above, in approximately equimolar amounts to yield a reaction mixture including compounds of the general formula of [III] and [IV]

$$\begin{array}{c} CH_3 \ \ R^* \\ | \ \ \ \ | \\ R-SiCH_2SnX, \\ | \ \ \ \ | \\ CH_3 \ \ R^* \end{array} \qquad [III]$$

$$\begin{array}{c} CH_3 \\ | \\ R-SiCH_2SnX_3 \\ | \\ CH_3 \end{array} \qquad [IV]$$

wherein R, R* and X are as defined above, and subsequently, without the isolation of the asymmetric triorganotin halide [III], reacting the reaction mixture with substantially twice the molar amount, based on monoorganotin trihalide [IV], of an either solution of an organomagnesium halide of the general formula of [V]

$$R^*MgX \qquad [V]$$

wherein R* and X are as defined above.

A summary of the process for the preparation of an asymmetric triorganotin halide of the present invention is as follows.

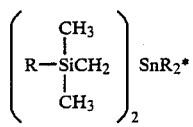

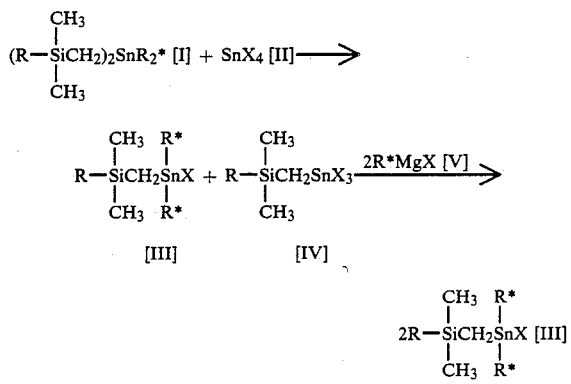

(wherein R, R* and X are as defined above).

The asymmetric tetraorganotin represented by the above general formula [I] can be produced in accordance with a known procedure by reacting one mole of diorganotin dihalide ($R_2^*SnX_2$) with two moles of organomagnesium halide including silicon

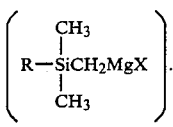

The redistribution reaction between an asymmetric tetraorganotin [I] and a tin (IV) halide [II] in the present invention is usually carried out in inert solvents or without solvents by employing the ratio of substantially from 0.8 to 1.2 moles, preferably from 0.95 to 1.05 moles of tin (IV) halide to one mole an asymmetric tetraorganotin [I].

Also, this reaction is an exothermic reaction and at a high temperature, a side reaction occurs and it lowers the yield of the proposed asymmetric triorganotin halide.

Therefore, it is preferable to add dropwise either of tin (IV) halide or asymmetric tetraorganotin without solvents or by dilution with an inert organic solvent to the other.

Examples of the inert organic solvents may include an aromatic hydrocarbon such as benzene, toluene, xylene, etc.; an aliphatic hydrocarbon such as n-hexane, n-heptane, cyclohexane, etc. and n-hexane or cyclohexane are preferably used.

The temperature of the dropwise addition and the reaction is maintained at from 0° to 120° C., preferably from 20° to 80 ° C. In the case of a higher temperature than this, there is fear of severing the secondary organo radical including silicon. Also, the time of dropwise addition and reaction is not restricted in particular but preferably the time of dropwise addition is from 0.5 to 1 hour and the time of the reaction is from 0.5 to 4 hours. When in accordance with this procedure the redistribution reaction is carried out, an asymmetric triorganotin halide [III] and monoorganotin trihalide are prepared at a ratio of about 1:1 (molar ratio).

Then a single product of an asymmetric triorganotin halide [III]can be obtained by the reaction of a reaction mixture solution including an asymmetric triorganotin halide [III] and a monoorganotin trihalide [IV] with substantially twice the molar amounts based on monoorganotin trihalide [IV] of a particular organomagnesium halide [V].

In this reaction, as the organomagnesium halide does not affect an asymmetric triorganotin halide, it is considered that the yield of a single product of an asymmetric triorganotin halide results from the reaction of an organomagnesium halide with only the monoorganotin trihalide.

The ether solution of organomagnesium halide represented by the above general formula V] can be obtained by the reaction of an organo halide with a magnesium in ether. The ether used in this reaction is, for example, five-membered or six-membered cyclic ether such as tetrahydrofuran, tetrahydropyran, 2-methyl tetrahydrofuran, 2-ethoxy tetrahydrofuran, tetrahydrofurfuryl ethyl ether, N-methyl morpholine, dioxane, etc.; an aliphatic ether, for example, such as diethyl ether, dibutyl ether, diethylene glycol dimethyl ether, ethylene glycol dibutyl ether, etc. is usable.

Because it is preferable to use an organomagnesium halide as a solution of a complex with ether, the use of the above cyclic ether which easily forms the complex, is suitable for this purpose. The amount of ether used is at least two moles per mole of organomagnesium halide, and preferably can be used in the range of from 3 to 6 moles per mole of organomagnesium halide.

In this invention the amount of the above organomagnesium halide which is allowed to react with the mixed solution of an asymmetric triorganotin halide [III] and monoorganotin trihalide [IV] must be substantially two moles per mole of monoorganotin trihalide [IV]. Therefore, an organomagnesium halide is usually usable in the range of from 160 to 240 mole %, preferably 190 to 210 mole %, based on monoorganotin trihalide.

Either the mixed solution including an asymmetric triorganotin halide and a monoorganotin trihalide or the ether solution of organomagnesium halide must be added dropwise to the other because the reaction of organomagnesium halide with monoorganotin trihalide is an exothermic reaction. In order to run the reaction smoothly it is preferable that the ether solution of the organomagnesium halide is added dropwise.

The present invention is usually carried out as follows.

The ether solution of substantially two moles of organomagnesium halide per mole of monoorganotin trihalide is added dropwise to the mixed solution including at the ratio about 1:1 (molar ratio) of an asymmetric triorganotin halide and monoorganotin trihalide obtained by the reaction of an asymmetric tetraorganotin with tin (IV) halide.

Said dropwise addition is performed while maintaining a temperature of 20 to 60° C. over about 0.5 to 2 hours.

If the temperature is higher than this, there is fear of producing the undesirable tetraorganotin form by the further action of an organomagnesium halide. After the addition, the mixture is heated and allowed to react at a temperature of 60 to 100° C. at which the solvent refluxes slowly for 0.5 to 4 hours.

The reaction mixture is hydrolyzed in an aqueous acid solution. The organic layer is separated and the solvent is removed to yield a single product of an asymmetric triorganotin halide in a high yield and high purity. If necessary, the obtained asymmetric triorganotin halide can be further purified by solution in an alcohol such as methanol, ethanol, etc. or an aliphatic hydrocarbon such as n-hexane, n-heptane, etc. or the mixed solvent thereof and then recrystallization or by column chromatography.

Representative examples of an asymmetric triorganotin halides obtained in accordance with the process of the present invention are as follows.

Dicyclohexyl (trimethylsilylmethyl)tin chloride or bromide,

Dicyclohexyl (ethyldimethylsilylmethyl)tin chloride or bromide,

Dicyclohexyl (isopropyldimethylsilylmethyl)tin chloride or bromide,

Dicyclohexyl (n-butyldimethylsilylmethyl)tin chloride or bromide,

Dicyclohexyl (n-octyldimethylsilylmethyl)tin chloride or bromide,

Dicyclohexyl (phenyldimethylsilylmethyl)tin chloride or bromide,

Dineophyl (trimethylsilylmethyl)tin chloride or bromide,

Dineophyl (ethyldimethylsilylmethyl)tin chloride or bromide,

Dineophyl (isopropyldimethylsilylmethyl)tin chloride or bromide,

Dineophyl (n-butyldimethylsilylmethyl)tin chloride or bromide,

Dineophyl (n-octyldimethylsilylmethyl)tin chloride or bromide, and

Dineophyl (phenyldimethylsilylmethyl)tin chloride or bromide.

According to the process of this invention, the route to the end product of asymmetric triorganotin halides does not have to involve isolation of the monoorganotin trihalide obtained as a by-product during the reaction of asymmetric tetraorganotin with tin (IV) halide. The reaction mixture can be all but completely converted into a single uniform pure product of asymmetric triorganotin halide by adding organomagnesium halide to the same reaction system.

Also according to the present invention the reaction steps can be shortened considerably because all steps can be performed continuously in the same reaction vessel.

The above asymmetric triorganotin halide has biological activity per se and can effectively protect plants from damage by mites.

[EXAMPLE]

The following examples illustrate the present invention. % in the examples indicates % by weight.

REFERENCE EXAMPLE

The preparation of dineophyl-di(trimethylsilylmethyl)tin

A 2-liter four-necked flask equipped with a stirrer, a thermometer, a dropping funnel and a condenser with a device for introduction of nitrogen was charged with magnesium strips (24.3 g, 1.0 mol), trimethylsilylmethyl chloride (5 g) and tetrahydrofuran (5 g) and then was heated after addition of n-butyl bromide as a reaction initiator.

When the inner temperature reached 60° to 70° C., white smoke was observed and the reaction began, whereupon stirring was started. After the temperature stopped rising, a mixed solution of trimethylsilylmethyl chloride (117.7 g, 0.959 mol) and tetrahydrofuran (300 g) was added dropwise from a dropping funnel over about 1 hour at the speed at which a tetrahydrofuran was refluxed slowly without external heating. After completion of the addition, the reaction mixture was heated under reflux for 3 hours and then cooled. When the inner temperature reached 20° to 30° C. a solution of dineophytin dichloride (218.9 g, 0.48 mol) dissolved in benzene (300 g) was dropwise added while maintaining the inner temperature of 20° to 50° C. After the addition, the reaction mixed solution was heated and reacted for 3 hours at the temperature of reflux. The reaction mixture was then cooled to 30° C. or below and 10 % aqueous hydrochloric acid solution (300 g) was added.

After 10 minutes' stirring, the organic layer was separated by a separating funnel, filtered and the solvent was removed under reduced pressure to give an oily dineophyl-di(trimethylsilylmethyl)tin (272.4 g) having $n_D^{30}$:1.5352. Purity by gas chromatography was 98.6%.

Another asymmetric tetraorganotin was prepared in the same way as in the reference example.

EXAMPLE 1

The preparation of dineophyl (trimethylsilylmethyl)tin chloride (1) The preparation of neophylmagnesium chloride A 1-liter four-necked flask equipped with a stirrer, a thermometer, a dropping funnel and a condenser with an apparatus for introduction of nitrogen was charged with magnesium strips (24.3 g, 1.0 mol), neophyl chloride (5 g) and tetrahydrofuran (5 g), and then was heated after the addition of n-butyl bromide as a reaction initiator. As the white smoke was observed and the reaction began when the temperature reached 60° to 70° C., stirring was started.

After the temperature rise stopped, the mixed solution of neophyl chloride (163.6 g, 0.97 mol) and tetrahydrofuran (295 9, 4.1 mol) was added dropwise from a dropping funnel over about 1 hour at the speed which a tetrahydrofuran was refluxed slowly by the reaction heat without the outside heat.

After completion of the addition, the reaction mixture was heated under reflux for 3 hours and then cooled to 20° to 30° C. An obtained neophylmagnesium chloride solution (Grignard reagent) with a dark brown clear liquid and magnesium strips were completely consumed.

(2) The preparation of dineophyl (trimethylsilylmethyl)tin chloride

A 3-liter four-necked flask equipped with a stirrer, a thermometer, a dropping funnel and a condenser with an apparatus for introduction of nitrogen was charged with dineophyl-di(trimethylsilylmethyl)tin (233.8 g 0.4 mol) obtained in reference example and cyclohexane (600 g ) and the inner atmosphere thereof was replaced with nitrogen gas. Anhydrous tin (IV) chloride (104.2 g, 0.4 mol) was dropwise added from a dropping funnel while cooling and maintaining the temperature of 20° to 50° C. over about 1 hour.

After completion of addition, a reaction mixture was heated at the temperature of 50° to 60° C. for 3 hours and the reaction was allowed to go to completion.

Analysis by gas chromatography of this reaction mixture indicated that it included 61.5% of dineophyl (trimethylsilylmethyl)tin chloride (0.397 mol) and 37.8% of trimethylsilylmethyltin trichloride (0.397 mol).

Continuously without isolation or purification of this reaction mixture, tetrahydrofuran solution of neophylmagnesium chloride (405.1 g, 0.794 mol) obtained in the above (1) was added dropwise into this reaction mixed solution from a dropping funnel while maintaining the temperature at 20° to 40° C. over about 1 hour. After completion of addition, the reaction mixed solution was heated under reflux for 3 hours. The reaction mixture was cooled to 30° C. or below and hydrolyzed by the addition of 10% aqueous hydrochloric acid solution. The organic layer was then separated and filtered. Cyclohexane and tetrahydrofuran were removed under reduced pressure to give dineophyl (trimethylsilylmethyl)tin chloride (405.4 g, yield 97.1%) having a melting point of 41° to 43° C. Analysis by gas chromatography of this material indicated 97.3% purity. The material was purified by recrystallization from methanol to give m.p.: 42.5° to 43.5° C., purity: 99.1% (by gas chromatography) and chlorine content: 7.1% (calculated value 7.0%).

EXAMPLE 2

The preparation of dineophyl (phenyldimethylsilylmethyl)tin chloride

An anhydrous tin (IV) chloride (104.2 g, 0.4 mol) was reacted with and treated by substantially the same procedure as in Example 1-(2) except that dineophyldi(-phenyldimethylsilylmethyl)tin ($n_D^{30}$: 1.5756, 273.5 g, 0.4 mol) was used instead of dineophyl di-(trimethylsilylmethyl) (tin (223.8 g, 0.4 mol) in Example 1-(2).

Analysis by gas chromatography of the obtained reaction mixture indicated that it included 59.8% of dineophyl (phenyldimethylsilylmethyl)tin chloride (0.396 mol) and 39.2% of phenyldimethylsilylmethyltin trichloride (0.396 mol).

Continuously without an isolation or purification of this reaction mixture, a tetrahydrofuran solution of neophylmagnesium chloride (404.1 g, 0.792 mol) was reacted with this reaction mixture and treated by substantially the same procedure as in Example 1-(2) to give dineophyl (phenyldimethylsilylmethyl)tin chloride (451.7 g, yield 96.5%) having a melting point of 26° to 28° C.

Analysis by gas chromatography of this material indicated 97.4% purity.

The material was purified by recrystallization from methanol to give m.p.: 28° to 29° C., purity: 99.7% (by gas chromatography) and chlorine content: 6.3% (calculated value 6.2%).

EXAMPLE 3

The preparation of dicyclohexyl (trimethylsilylmethyl)tin chloride (1) The preparation of cyclohexylmagnesium chloride A cyclohexylmagnesium chloride solution (Grignard reagent) was prepared by substantially the same procedure as in Example 1-(1) except that cyclohexyl chloride (118.6 g, 1.0 mol) was used instead of neophyl chloride (168.6 g, 1.0 mol) in Example 1-(1).

(2) The preparation of dicyclohexyl (trimethylsilylmethyl) tin chloride

An anhydrous tin (IV) chloride (104.2 g, 0.4 mol) was reacted with and treated by substantially the same procedure as in Example 1-(2) except that dicyclohexyl-di (trimethylsilylmethyl)tin (m.p.: 58.6° C., 183.8 g, 0.4 mol) was used instead of dineophyl-di(trimethylsilylmethyl)tin (223.8 g, 0.4 mol) in Example 1-(2).

Analysis by gas chromatography of the obtained reaction mixture indicated that it included 56.2% of dicyclohexyl (trimethylsilylmethyl)tin chloride (0.397 mol) and 43.0% of trimethylsilylmethyltin trichloride (0.396 mol).

Continuously without isolation or purification of this reaction mixture, a tetrahydrofuran solution of cyclohexylmagnesium chloride (369.2 g, 0.792 mol) obtained above (1) was reacted with this reaction mixture and treated by substantially the same procedure as in Example 1-(2) to give dicyclohexyl (trimethylsilylmethyl)tin chloride with a melting point of 70° to 73° C. (324.5 g, yield 96.0%).

Analysis by gas chromatography of this material indicated 96.5% purity.

The material was purified by recrystallization from methanol to give m.p.: 74° C., purity: 99.0% (by gas chromatography) and chlorine content: 8.8% (calculated value 8.7%).

EXAMPLE 4

The preparation of dicyclohexyl (phenyldimethylsilylmethyl) tin chloride

An anhydrous tin (IV) chloride (104.2 g, 0.4 mol) was reacted with and treated by substantially the same procedure as in Example 1-(2) except that dicyclohexyl-di (phenyldimethylsilylmethyl)tin $n_D^{30}$: 1.5612, 233.4 g, 0.4 mol) was used instead of dineophyl-di(trimethylsilylmethyl)tin (223.8 g, 0.4 mol) in Example 1-(2).

Analysis by gas chromatography of the obtained reaction mixture indicated that it included 55.1% of dicyclohexyl (phenyldimethylsilylmethyl)tin chloride (0.396 mol) and 43.9% of phenyldimethylsilylmethyltin trichloride (0.396 mol).

Continuously without an isolation or purification of this reaction mixture, a tetrahydrofuran solution of cyclohexylmagnesium chloride (369.2 g, 0.792 mol) was reacted with this reaction mixture and treated by substantially the same procedure as in Example 1-(2) to give oily dicyclohexyl (phenyldimethylsilylmethyl)tin chloride (372.4 g, yield 96.8%).

Analysis by gas chromatography of this material indicated 96.7% purity.

The material was purified by column chromatography to give a refractive index of $n_D^{30}$: 1.5593, purity: 99.1% (by gas chromatography) and chlorine content: 7.6% (calculated value 7.5%).

COMPARATIVE EXAMPLE 1

The preparation of di-n-butyl (trimethylsilylmethyl) tin chloride

An anhydrous tin (IV) chloride (104.2 g, 0.4 mol) was reacted with and treated by substantially the same procedure as in Example 1-(2) except that di-n-butyl-di(trimethylsilylmethyl)tin (104.2 g, 0.4 mol) was used instead of dineophyl-di(trimethylsilylmethyl)tin (223.8 g, 0.4 mol) in Example 1-(2).

Analysis by gas chromatography of the obtained reaction mixture indicated that it included 25.3% of di-n-butyl (trimethylsilylmethyl)tin chloride, 22.2% of trimethylsilylmethyltin trichloride, 30.3% of n-butyl-di(trimethylsilylmethyl)tin chloride (by-product) and 22.2% of mono-n-butyltin trichloride (by-product).

COMPARATIVE EXAMPLE 2

The preparation of di-n-butyl (trimethylsilylmethyl) tin chloride (1) The preparation of n-butylmagnesium chloride A n-butylmagnesium chloride solution (Grignard reagent) was prepared by substantially the same procedure as in Example 1-(1) except that n-butyl chloride (92.6 g, 1.0 mol) was used instead of neophyl chloride (168.6 g, 1.0 mol) in Example 1-(1).

(2) The preparation of di-n-butyl (trimethylsilylmethyl) tin chloride

A 3-liter four-necked flask equipped with a stirrer, a thermometer, a dropping funnel and a condenser with an apparatus for introduction of nitrogen was charged with di-n-butyl (trimethylsilylmethyl)tin chloride (142.2 g, 0.4 mol), trimethylsilylmethyltin trichloride (124.9 g, 0.4 mol) and cyclohexane (600 g), and stirred.

A tetrahydrofuran solution of n-butylmagnesium chloride (343.8 g, 0.8 mol) obtained in the above (1) was reacted with this mixture and treated by substantially the same procedure as in Example 1-(2) to give oily condensed material (284.5 g).

Analysis by gas chromatography of this oily condensed material obtained indicated that it included 37.5% of di-n-butyl (trimethylsilylmethyl)tin chloride, 11.0% of trimethylsilylmethyltin trichloride, 11.7% of n-butyl (trimethylsilylmethyl)tin dichloride and 39.8% of tri-n-butyl (trimethylsilylmethyl)tin.

EXAMPLE 5

The preparation of dineophyl (trimethylsilylmethyl) tin bromide (1) The preparation of neophylmagnesium bromide A neophylmagnesium bromide solution (Grignard reagent) was prepared by substantially the same procedure as in Example 1-(1) except that neophyl bromide (213.1 g, 1.0 mol) was used instead of neophyl chloride (168.6 g, 1.0 mol) in Example 1-(1) and a dropwise addition and reaction temperature was run 40° C. or below.

Analysis of 100 g of this Grignard reagent indicated the content of neophylmagnesium bromide corresponding 0.176 mol.

(2) The preparation of dineophyl (trimethylsilylmethyl) tin bromide

A 3-liter four-necked flask equipped with a stirrer, a thermometer, a dropping funnel and a condenser with an apparatus for introduction of nitrogen was charged with anhydrous tin (IV) bromide (175.3 g, 0.4 mol) and cyclohexane (600 g), and stirred under a stream of nitrogen. Dineophyl-di(trimethylsilylmethyl)tin (223.8 g, 0.4 mol) was added dropwise from a dropping funnel while maintaining the temperature at 20° to 50° C. over about 1 hour.

The inside of the dropping funnel was washed with a small amount of cyclohexane and added to the mixture. After completion of addition, the reaction mixture was heated at the temperature of 50° to 60° C. for 3 hours and the reaction was allowed to go to completion.

Analysis by gas chromatography of this reaction mixture indicated that it included 54.6% of dineophyl (trimethylsilylmethyl)tin bromide (0.395 mol) and 44.1% of trimethylsilylmethyltin tribromide (0.395 mol).

Continuously without isolation or purification of this reaction mixture, tetrahydrofuran solution of neophylmagnesium bromide (448.9 g, 0.790 mol) obtained in the above (1) was added dropwise into this reaction mixture solution from a dropping funnel while maintaining the temperature at 20° to 40° C. over about 1 hour.

After completion of addition, the reaction mixture solution was heated under reflux for 3 hours and then cooled to 30° C. or below and hydrolyzed by the addition of 10% aqueous hydrobromic acid solution (550 g). The organic layer was separated by a separating funnel, filtered and cyclohexane and tetrahydrofuran were removed under reduced pressure to give dineophyl (trimethylsilylmethyl)tin bromide (440.9 g, yield 97.0%) with m.p.: 36° to 38° C.

Analysis by gas chromatography of this material indicated 97.2% purity. The this material was purified by recrystallization from methanol to give m.p.: 38 to 39° C., purity: 99.1% (by gas chromatography) and bromine content: 14.6% (calculated value 14.5%).

We claim:

1. A process for the preparation of an asymmetric triorganotin halide represented by the formula III

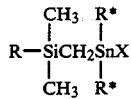

wherein R represent alkyl or phenyl, R* represents cyclohexyl or neophyl, and X represents a chlorine or bromine atom,
which comprises reacting in the presence or absence of an inert organic solvent an asymmetric tetraorganotin compound of the formula I

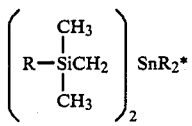

wherein R and R* are as defined above, with a tin (IV) halide of the formula II $$SnX_4 \qquad \text{II}$$

wherein X is as defined above, in approximately equimolar amounts to yield a reaction mixture including an asymmetric triorganotin halide compound of the formula III and a monoorganotin trihalide compound of the formula IV

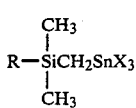

wherein R, R* and X are as defined above, and subsequently, without isolating the asymmetric triorganotin halide III, reacting the reaction mixture with substantially twice the molar amount, based on monoorganotin trihalide IV, of an ether solution of an organomagnesium halide of the formula V $$R^*MgX \qquad \text{V}$$

wherein R* and X are as defined above.

2. The process of claim 1 in which the reaction of an asymmetric tetraorganotin [I] with tin (IV) halide is carried out at a temperature of 20° to 80° C.

3. The process of claim 1 in which the reaction of monoorganotin trihalide [IV] with organomagnesium halide is carried out at a temperature of 20° to 60° C.

4. The process of claim 1 in which R is methyl of phenyl.

5. The process of claim 1 in which X is chlorine.

* * * * *